(12) United States Patent
Farnan

(10) Patent No.: US 11,571,554 B2
(45) Date of Patent: Feb. 7, 2023

(54) BALLOON CATHETER WITH NON-DEPLOYABLE STENT

(75) Inventor: Robert C. Farnan, Davie, FL (US)

(73) Assignee: ANGIOSCORE, INC., Fremont, CA (US)

( * ) Notice: Subject to any disclaimer, the term of this patent is extended or adjusted under 35 U.S.C. 154(b) by 0 days.

(21) Appl. No.: 13/489,250

(22) Filed: Jun. 5, 2012

(65) Prior Publication Data

US 2012/0245616 A1 Sep. 27, 2012

Related U.S. Application Data

(63) Continuation of application No. 13/022,489, filed on Feb. 7, 2011, now Pat. No. 10,086,178, which is a
(Continued)

(51) Int. Cl.
*A61M 29/00* (2006.01)
*A61M 25/10* (2013.01)
(Continued)

(52) U.S. Cl.
CPC ... *A61M 25/104* (2013.01); *A61B 17/320725* (2013.01); *A61F 2/91* (2013.01);
(Continued)

(58) Field of Classification Search
CPC ........... A61B 2017/320004; A61B 17/320725; A61B 17/22; A61B 17/221; A61B 17/3207; A61B 2017/320024; A61B 2017/22051; A61B 2017/22061; A61B 2017/320008; A61B 2018/00214; A61B 2017/00858;
(Continued)

(56) References Cited

U.S. PATENT DOCUMENTS 2,701,559 A * 2/1955 Cooper .................... 600/569
2,854,983 A * 10/1958 Baskin ................. 604/103.11
(Continued)

FOREIGN PATENT DOCUMENTS

EP 0565796 B1 5/1997
EP 0623315 B1 6/1999
(Continued)

OTHER PUBLICATIONS

PCT Search Report for International Application No. PCT/US04/27836, dated Dec. 30, 2004 by Jackie Tan-Uyen T. Ho.
(Continued)

*Primary Examiner* — Darwin P Erezo
*Assistant Examiner* — Erin L Colello

(57) ABSTRACT

An angioplasty balloon including a non-deployable stent to prevent or reduce the potential for slippage of the inflated balloon with respect to the vessel wall being treated. The balloon includes a non-deployable stent that is adapted to be secured to the balloon or angioplasty balloon catheter. The stent has a proximal end, a distal end, and at least three radially-spaced struts, each, each strut connecting the proximal end to the distal end and having one or more bends that allow expansion of the strut to accommodate the inflation of the balloon. The stem is made or a material so that the stent collapses upon deflation of the balloon.

18 Claims, 13 Drawing Sheets

Related U.S. Application Data continuation of application No. 11/292,426, filed on Dec. 1, 2005, now Pat. No. 7,931,663, which is a continuation of application No. 10/651,557, filed on Aug. 29, 2003, now abandoned, which is a continuation-in-part of application No. 10/399,589, filed as application No. PCT/US02/35547 on Nov. 6, 2002, now Pat. No. 7,691,119.

(60) Provisional application No. 60/344,982, filed on Nov. 9, 2001.

(51) Int. Cl.
　　*A61B 17/3207* (2006.01)
　　*A61F 2/91* (2013.01)
　　*A61F 2/915* (2013.01)
　　*A61F 2/958* (2013.01)
　　*A61B 17/00* (2006.01)
　　*A61B 17/22* (2006.01)

(52) U.S. Cl.
　　CPC .............. *A61F 2/915* (2013.01); *A61F 2/958* (2013.01); *A61M 25/10* (2013.01); *A61M 25/1027* (2013.01); *A61B 2017/00858* (2013.01); *A61B 2017/22061* (2013.01); *A61F 2002/91525* (2013.01); *A61F 2002/91533* (2013.01); *A61F 2002/91558* (2013.01); *A61F 2210/0076* (2013.01); *A61F 2230/005* (2013.01); *A61F 2230/0058* (2013.01); *A61F 2230/0067* (2013.01); *A61M 2025/105* (2013.01); *A61M 2025/109* (2013.01); *A61M 2025/1081* (2013.01); *A61M 2025/1086* (2013.01); *A61M 2025/1088* (2013.01)

(58) Field of Classification Search
　　CPC .... A61M 2025/109; A61M 2025/1084; A61M 2025/1086; A61M 25/104; A61M 25/10; A61M 2025/1081; A61M 2025/1088; A61M 2025/1068; A61M 25/1027; A61M 2025/105; A61F 2/90; A61F 2/86; A61F 2/958; A61F 2002/9583; A61F 2/89; A61F 2/915; A61F 2002/91508–91575; A61F 2002/9505; A61F 2002/9155; A61F 2002/9623; A61F 2002/9586; A61F 2/966–9662; A61F 2/962; A61F 2/91; A61F 2002/91525; A61F 2002/91533; A61F 2002/91558; A61F 2210/0076; A61F 2230/005; A61F 2230/0058; A61F 2230/0067
　　USPC ...... 623/1.11, 1.17; 606/194, 191, 192, 159; 604/103, 103.05, 103.07, 103.08, 103.09, 604/104, 509

See application file for complete search history.

(56) References Cited

U.S. PATENT DOCUMENTS

| | | | |
|---|---|---|---|
| 3,045,677 A | 7/1962 | Wallace | |
| 3,467,101 A | 9/1969 | Fogarty et al. | |
| 3,825,013 A | 7/1974 | Craven | |
| 4,327,736 A | 5/1982 | Inoue | |
| 4,456,011 A | 6/1984 | Warnecke | |
| 4,483,340 A | 11/1984 | Fogarty et al. | |
| 4,604,762 A | 8/1986 | Robinson | |
| 4,637,396 A | 1/1987 | Cook | |
| 4,649,922 A | 3/1987 | Wiktor | |
| 4,723,549 A | 2/1988 | Wholey et al. | |
| 4,733,665 A | 3/1988 | Palmaz | |
| 4,796,629 A | 1/1989 | Grayzel | |
| 4,838,853 A | 6/1989 | Parisi | |
| 4,887,613 A | 12/1989 | Farr et al. | |
| 4,895,166 A | 1/1990 | Farr et al. | |
| 4,921,484 A | 5/1990 | Hillstead | |
| 4,942,788 A | 7/1990 | Farr et al. | |
| 4,950,227 A | 8/1990 | Savin et al. | |
| 4,956,830 A | 9/1990 | Mock et al. | |
| 4,969,458 A | 11/1990 | Wiktor | |
| 4,976,711 A | 12/1990 | Parins et al. | |
| 4,986,807 A | 1/1991 | Farr | |
| 4,986,830 A | 1/1991 | Owens et al. | |
| 4,998,539 A * | 3/1991 | Delsanti .................. | 128/898 |
| 5,003,918 A | 4/1991 | Olson et al. | |
| 5,019,088 A | 5/1991 | Farr | |
| 5,019,089 A | 5/1991 | Farr | |
| 5,026,384 A | 6/1991 | Farr et al. | |
| 5,062,384 A | 11/1991 | Foley et al. | |
| 5,062,648 A | 11/1991 | Gomringer | |
| 5,071,407 A | 12/1991 | Termin et al. | |
| 5,098,440 A | 3/1992 | Hillstead | |
| 5,100,386 A | 3/1992 | Inoue | |
| 5,100,423 A | 3/1992 | Fearnot | |
| 5,101,682 A | 4/1992 | Radisch et al. | |
| 5,102,402 A | 4/1992 | Dror et al. | |
| 5,102,417 A | 4/1992 | Palmaz | |
| 5,108,416 A | 4/1992 | Ryan et al. | |
| 5,112,345 A | 5/1992 | Farr | |
| 5,116,318 A | 5/1992 | Hillstead | |
| 5,120,322 A | 6/1992 | Davis et al. | |
| 5,133,732 A | 7/1992 | Wiktor | |
| 5,176,693 A * | 1/1993 | Pannek, Jr. ............... | 606/159 |
| 5,181,911 A | 1/1993 | Shturman | |
| 5,190,058 A | 3/1993 | Jones et al. | |
| 5,192,291 A | 3/1993 | Pannek et al. | |
| 5,196,024 A | 3/1993 | Barath | |
| 5,209,727 A | 5/1993 | Radisch et al. | |
| 5,222,971 A | 6/1993 | Willard et al. | |
| 5,224,945 A | 7/1993 | Pannek et al. | |
| 5,224,949 A | 7/1993 | Gomringer et al. | |
| 5,226,887 A | 7/1993 | Farr et al. | |
| 5,243,997 A | 9/1993 | Uflacker et al. | |
| 5,263,963 A | 11/1993 | Garrison et al. | |
| 5,295,493 A | 3/1994 | Radisch et al. | |
| 5,295,959 A * | 3/1994 | Gurbel ................. | A61M 25/104 604/103 |
| 5,304,121 A | 4/1994 | Sahatjian | |
| 5,306,250 A | 4/1994 | March et al. | |
| 5,308,354 A | 5/1994 | Zacca et al. | |
| 5,308,356 A * | 5/1994 | Blackshear, Jr. . | A61M 25/1002 604/101.01 |
| 5,318,576 A | 6/1994 | Plassche et al. | |
| 5,320,634 A | 6/1994 | Vigil et al. | |
| 5,336,178 A * | 8/1994 | Kaplan ................. | A61B 8/12 604/103.01 |
| 5,336,234 A | 8/1994 | Vigil et al. | |
| 5,344,401 A | 9/1994 | Radisch et al. | |
| 5,344,419 A | 9/1994 | Spears | |
| 5,350,101 A | 9/1994 | Godlewski | |
| 5,423,745 A | 6/1995 | Todd et al. | |
| 5,443,078 A | 8/1995 | Uflacker | |
| 5,443,446 A | 8/1995 | Shturman | |
| 5,443,496 A | 8/1995 | Schwartz et al. | |
| 5,449,372 A * | 9/1995 | Schmaltz .................. | A61F 2/88 604/104 |
| 5,449,373 A | 9/1995 | Pinchasik et al. | |
| 5,456,666 A | 10/1995 | Campbell et al. | |
| 5,456,667 A * | 10/1995 | Ham et al. .................. | 604/107 |
| 5,458,568 A | 10/1995 | Racchini et al. | |
| 5,460,607 A | 10/1995 | Miyata et al. | |
| 5,470,314 A | 11/1995 | Walinsky | |
| 5,501,694 A | 3/1996 | Ressemann et al. | |
| 5,524,635 A | 6/1996 | Uflacker et al. | |
| 5,527,282 A | 6/1996 | Segal | |
| 5,536,178 A | 7/1996 | Novelli | |
| 5,545,132 A | 8/1996 | Fagan et al. | |
| 5,556,405 A | 9/1996 | Lary | |
| 5,556,408 A | 9/1996 | Farhat | |
| 5,562,620 A | 10/1996 | Klein et al. | |
| 5,569,195 A | 10/1996 | Saab | |

(56) References Cited

U.S. PATENT DOCUMENTS

| | | | |
|---|---|---|---|
| 5,571,086 A * | 11/1996 | Kaplan et al. | 604/96.01 |
| 5,607,442 A | 3/1997 | Fischell et al. | |
| 5,609,574 A | 3/1997 | Kaplan et al. | |
| 5,616,149 A | 4/1997 | Barath | |
| 5,620,457 A | 4/1997 | Pinchasik et al. | |
| 5,624,433 A | 4/1997 | Radisch et al. | |
| 5,628,746 A | 5/1997 | Clayman | |
| 5,628,755 A | 5/1997 | Heller et al. | |
| 5,643,210 A | 7/1997 | Iacob | |
| 5,649,941 A | 7/1997 | Lary | |
| 5,681,281 A | 10/1997 | Vigil et al. | |
| 5,690,642 A | 11/1997 | Osborne et al. | |
| 5,695,469 A | 12/1997 | Segal | |
| 5,697,944 A | 12/1997 | Lary | |
| 5,697,971 A | 12/1997 | Fischell et al. | |
| 5,702,410 A | 12/1997 | Klunder et al. | |
| 5,707,385 A | 1/1998 | Williams | |
| 5,713,863 A | 2/1998 | Vigil et al. | |
| 5,713,913 A | 2/1998 | Lary et al. | |
| 5,718,684 A * | 2/1998 | Gupta | 604/103.07 |
| 5,730,698 A * | 3/1998 | Fischell et al. | 600/3 |
| 5,733,303 A | 3/1998 | Israel et al. | |
| 5,735,816 A | 4/1998 | Lieber et al. | |
| 5,742,019 A | 4/1998 | Radisch et al. | |
| 5,755,708 A | 5/1998 | Segal | |
| 5,755,781 A | 5/1998 | Jayaraman | |
| 5,766,201 A | 6/1998 | Ravenscroft et al. | |
| 5,766,238 A | 6/1998 | Lau et al. | |
| 5,772,681 A | 6/1998 | Leoni | |
| 5,776,141 A * | 7/1998 | Klein et al. | 623/1.11 |
| 5,776,181 A | 7/1998 | Lee et al. | |
| 5,792,144 A | 8/1998 | Fischell et al. | |
| 5,792,415 A | 8/1998 | Hijlkema | |
| 5,797,935 A * | 8/1998 | Barath | 606/159 |
| 5,807,355 A | 9/1998 | Ramzipoor et al. | |
| 5,810,767 A | 9/1998 | Klein | |
| 5,814,061 A | 9/1998 | Osborne et al. | |
| 5,827,321 A | 10/1998 | Roubin et al. | |
| 5,863,284 A * | 1/1999 | Klein | 600/3 |
| 5,868,708 A * | 2/1999 | Hart et al. | 604/104 |
| 5,868,719 A | 2/1999 | Tsukernik | |
| 5,868,779 A | 2/1999 | Ruiz | |
| 5,868,783 A | 2/1999 | Tower | |
| 5,869,284 A | 2/1999 | Cao et al. | |
| 5,891,090 A | 4/1999 | Thornton | |
| 5,902,475 A | 5/1999 | Trozera et al. | |
| 5,904,679 A | 5/1999 | Clayman | |
| 5,904,698 A * | 5/1999 | Thomas et al. | 606/159 |
| 5,906,639 A | 5/1999 | Rudnick et al. | |
| 5,916,166 A | 6/1999 | Reiss et al. | |
| 5,919,200 A | 7/1999 | Stambaugh et al. | |
| 5,954,742 A | 9/1999 | Osypka | |
| 5,961,490 A | 10/1999 | Adams | |
| 5,967,984 A | 10/1999 | Chu et al. | |
| 5,980,486 A | 11/1999 | Enger | |
| 5,987,661 A | 11/1999 | Peterson | |
| 5,994,667 A | 11/1999 | Merdan et al. | |
| 6,013,055 A | 1/2000 | Bampos et al. | |
| 6,022,359 A * | 2/2000 | Frantzen | A61F 2/958 606/108 |
| 6,036,686 A | 3/2000 | Griswold | |
| 6,036,689 A * | 3/2000 | Tu et al. | 606/41 |
| 6,036,708 A | 3/2000 | Van Sciver | |
| 6,048,356 A | 4/2000 | Ravenscroft et al. | |
| 6,053,913 A | 4/2000 | Tu et al. | |
| 6,059,811 A | 5/2000 | Pinchasik et al. | |
| 6,071,285 A | 6/2000 | Lashinski et al. | |
| 6,071,286 A | 6/2000 | Mawad | |
| 6,077,298 A | 6/2000 | Tu et al. | |
| RE36,764 E | 7/2000 | Zacca et al. | |
| 6,102,904 A | 8/2000 | Vigil et al. | |
| 6,106,548 A | 8/2000 | Roubin et al. | |
| 6,117,104 A | 9/2000 | Fitz | |
| 6,117,153 A | 9/2000 | Lary et al. | |
| 6,123,718 A | 9/2000 | Tu et al. | |
| 6,129,706 A | 10/2000 | Janacek | |
| 6,129,708 A | 10/2000 | Enger | |
| 6,136,011 A | 10/2000 | Stambaugh | |
| 6,146,323 A | 11/2000 | Fischell | |
| 6,152,944 A | 11/2000 | Holman et al. | |
| 6,156,254 A | 12/2000 | Andrews et al. | |
| 6,156,265 A | 12/2000 | Sugimoto | |
| 6,165,187 A | 12/2000 | Reger | |
| 6,190,356 B1 | 2/2001 | Bersin | |
| 6,190,403 B1 | 2/2001 | Fischell et al. | |
| 6,193,686 B1 | 2/2001 | Estrada et al. | |
| 6,203,569 B1 | 3/2001 | Wijay | |
| 6,206,910 B1 | 3/2001 | Berry et al. | |
| 6,210,392 B1 | 4/2001 | Vigil et al. | |
| 6,224,625 B1 | 5/2001 | Jayaraman | |
| 6,235,043 B1 | 5/2001 | Reiley et al. | |
| 6,241,762 B1 | 6/2001 | Shanley | |
| 6,245,040 B1 * | 6/2001 | Inderbitzen et al. | 604/103.07 |
| 6,258,087 B1 * | 7/2001 | Edwards et al. | 606/41 |
| 6,258,099 B1 | 7/2001 | Mareiro et al. | |
| 6,258,108 B1 | 7/2001 | Lary | |
| 6,261,319 B1 | 7/2001 | Kveen et al. | |
| 6,261,630 B1 | 7/2001 | Nazarova et al. | |
| 6,287,336 B1 | 9/2001 | Globerman et al. | |
| 6,289,568 B1 | 9/2001 | Miller et al. | |
| 6,296,651 B1 | 10/2001 | Lary et al. | |
| 6,306,151 B1 | 10/2001 | Lary | |
| 6,306,166 B1 * | 10/2001 | Barry et al. | 623/1.46 |
| 6,309,414 B1 | 10/2001 | Rolando et al. | |
| 6,312,459 B1 | 11/2001 | Huang et al. | |
| 6,319,229 B1 | 11/2001 | Kim et al. | |
| 6,319,242 B1 | 11/2001 | Patterson et al. | |
| 6,319,251 B1 | 11/2001 | Tu et al. | |
| 6,325,779 B1 | 12/2001 | Zedler | |
| 6,325,813 B1 | 12/2001 | Hektner | |
| 6,332,880 B1 | 12/2001 | Yang et al. | |
| 6,355,013 B1 | 3/2002 | van Muiden | |
| 6,355,059 B1 | 3/2002 | Richter et al. | |
| 6,361,545 B1 | 3/2002 | Macoviak et al. | |
| 6,364,856 B1 | 4/2002 | Ding et al. | |
| 6,371,961 B1 | 4/2002 | Osborne et al. | |
| 6,394,995 B1 | 5/2002 | Solar et al. | |
| 6,416,494 B1 | 7/2002 | Wilkins | |
| 6,416,539 B1 | 7/2002 | Hassdenteufel | |
| 6,425,882 B1 | 7/2002 | Vigil | |
| 6,425,908 B2 | 7/2002 | Ravenscroft et al. | |
| 6,440,158 B1 | 8/2002 | Saab | |
| 6,447,501 B1 | 9/2002 | Solar et al. | |
| 6,450,988 B1 | 9/2002 | Bradshaw | |
| 6,450,989 B2 | 9/2002 | Dubrul et al. | |
| 6,454,775 B1 | 9/2002 | Demarais et al. | |
| 6,471,979 B2 | 10/2002 | New et al. | |
| 6,475,233 B2 | 11/2002 | Trozera | |
| 6,475,234 B1 | 11/2002 | Richter et al. | |
| 6,475,236 B1 | 11/2002 | Roubin et al. | |
| 6,478,807 B1 | 11/2002 | Foreman et al. | |
| 6,500,186 B2 | 12/2002 | Lafontaine et al. | |
| 6,517,765 B1 | 2/2003 | Kelley | |
| 6,540,722 B1 | 4/2003 | Boyle et al. | |
| 6,551,310 B1 | 4/2003 | Ganz et al. | |
| 6,554,795 B2 | 4/2003 | Bagaoisan et al. | |
| 6,562,062 B2 | 5/2003 | Jenusaitis et al. | |
| 6,565,528 B1 | 5/2003 | Mueller | |
| 6,569,180 B1 | 5/2003 | Sirhan et al. | |
| 6,575,993 B1 | 6/2003 | Yock | |
| 6,585,757 B1 * | 7/2003 | Callol | A61F 2/90 623/1.34 |
| 6,592,548 B2 | 7/2003 | Jayaraman | |
| 6,602,281 B1 | 8/2003 | Klein | |
| 6,605,107 B1 | 8/2003 | Klein | |
| 6,607,442 B2 | 8/2003 | Ogata et al. | |
| 6,613,072 B2 | 9/2003 | Lau et al. | |
| 6,616,678 B2 | 9/2003 | Nishtala et al. | |
| 6,626,861 B1 | 9/2003 | Hart et al. | |
| 6,632,231 B2 | 10/2003 | Radisch et al. | |
| 6,648,912 B2 | 11/2003 | Trout, III et al. | |
| 6,652,548 B2 | 11/2003 | Evans et al. | |
| 6,656,351 B2 * | 12/2003 | Boyle | 210/136 |
| 6,663,660 B2 | 12/2003 | Dusbabek et al. | |

(56) References Cited

U.S. PATENT DOCUMENTS

| | | | |
|---|---|---|---|
| 6,695,813 B1 | 2/2004 | Boyle et al. | |
| 6,743,196 B2 | 6/2004 | Barbut et al. | |
| 6,746,463 B1 | 6/2004 | Schwartz | |
| 6,783,542 B2 | 8/2004 | Eidenschink | |
| 6,840,950 B2 | 1/2005 | Stanford et al. | |
| 6,872,206 B2 | 3/2005 | Edwards et al. | |
| 6,918,920 B1 | 7/2005 | Wang et al. | |
| 6,939,320 B2 | 9/2005 | Lennox | |
| 6,942,680 B2 | 9/2005 | Grayzel et al. | |
| 6,951,566 B2 | 10/2005 | Lary | |
| 7,011,654 B2 | 3/2006 | Dubrul et al. | |
| 7,011,670 B2 | 3/2006 | Radisch et al. | |
| 7,029,483 B2 | 4/2006 | Schwartz | |
| 7,060,051 B2 | 6/2006 | Palasis | |
| 7,131,981 B2 | 11/2006 | Appling et al. | |
| 7,172,609 B2 | 2/2007 | Radisch et al. | |
| 7,186,237 B2 | 3/2007 | Meyer et al. | |
| 7,232,432 B2 | 6/2007 | Fulton et al. | |
| 7,252,650 B1 | 8/2007 | Andrews et al. | |
| 7,303,572 B2 | 12/2007 | Melsheimer et al. | |
| 7,354,445 B2 | 4/2008 | Nicholson et al. | |
| 7,357,813 B2 | 4/2008 | Burgermeister | |
| 7,396,358 B2 | 7/2008 | Appling et al. | |
| 7,455,652 B2 | 11/2008 | Laird | |
| 7,465,311 B2 | 12/2008 | Wang et al. | |
| 7,494,497 B2 | 2/2009 | Weber | |
| 7,517,352 B2 | 4/2009 | Evans et al. | |
| 7,524,319 B2 | 4/2009 | Dubrul | |
| 7,566,319 B2 | 7/2009 | McAuley et al. | |
| 7,686,824 B2* | 3/2010 | Konstantino et al. | 606/194 |
| 7,691,119 B2 | 4/2010 | Farnan | |
| 7,708,748 B2 | 5/2010 | Weisenburgh, II et al. | |
| 7,708,753 B2 | 5/2010 | Hardert | |
| 7,736,375 B2 | 6/2010 | Crow | |
| 7,763,043 B2 | 7/2010 | Goodin et al. | |
| 7,780,715 B2 | 8/2010 | Shaked et al. | |
| 7,780,798 B2 | 8/2010 | Stinson et al. | |
| 7,931,663 B2 | 4/2011 | Farnan et al. | |
| 7,955,350 B2 | 6/2011 | Konstantino et al. | |
| 7,963,942 B2 | 6/2011 | Chen | |
| 7,976,557 B2 | 7/2011 | Kunis | |
| 7,998,184 B2 | 8/2011 | Eidenschink | |
| 8,043,259 B2 | 10/2011 | Radisch et al. | |
| 8,052,703 B2 | 11/2011 | St. Martin et al. | |
| 8,066,726 B2* | 11/2011 | Kelley | 606/159 |
| 8,080,026 B2 | 12/2011 | Konstantino et al. | |
| 8,123,770 B2 | 2/2012 | Olsen et al. | |
| 8,192,675 B2 | 6/2012 | Burton et al. | |
| 8,221,444 B2 | 7/2012 | Wang et al. | |
| 8,323,307 B2 | 12/2012 | Hardert | |
| 8,348,987 B2 | 1/2013 | Eaton | |
| 8,382,820 B2 | 2/2013 | Addonizio et al. | |
| 8,454,637 B2 | 6/2013 | Aggerholm et al. | |
| 8,574,248 B2 | 11/2013 | Kassab | |
| 8,685,050 B2 | 4/2014 | Schur et al. | |
| 8,685,990 B2 | 4/2014 | Coats et al. | |
| 9,199,066 B2 | 12/2015 | Konstantino et al. | |
| 9,351,756 B2 | 5/2016 | Gershony et al. | |
| 9,364,254 B2 | 6/2016 | Gershony et al. | |
| 9,375,328 B2 | 6/2016 | Farnan | |
| 2001/0001113 A1* | 5/2001 | Lim et al. | 604/96.01 |
| 2001/0001823 A1 | 5/2001 | Ryan | |
| 2001/0007082 A1 | 7/2001 | Dusbabek et al. | |
| 2001/0012950 A1 | 8/2001 | Nishtala et al. | |
| 2001/0016753 A1 | 8/2001 | Caprio et al. | |
| 2001/0031981 A1* | 10/2001 | Evans | A61B 17/221 606/200 |
| 2002/0010487 A1 | 1/2002 | Evans et al. | |
| 2002/0010489 A1* | 1/2002 | Grayzel | A61F 2/958 606/194 |
| 2002/0029015 A1 | 3/2002 | Camenzind et al. | 604/97.02 |
| 2002/0038144 A1 | 3/2002 | Trout, III et al. | |
| 2002/0045930 A1 | 4/2002 | Burg et al. | |
| 2002/0065548 A1 | 5/2002 | Birdsall et al. | |
| 2002/0077606 A1* | 6/2002 | Trotta | 604/264 |
| 2002/0111633 A1 | 8/2002 | Stoltze et al. | |
| 2002/0165599 A1 | 11/2002 | Nasralla | |
| 2002/0193873 A1 | 12/2002 | Brucker et al. | |
| 2003/0018376 A1 | 1/2003 | Solar et al. | |
| 2003/0023200 A1 | 1/2003 | Barbut et al. | |
| 2003/0028235 A1 | 2/2003 | McIntosh et al. | |
| 2003/0032973 A1 | 2/2003 | Jenusaitis et al. | |
| 2003/0065381 A1 | 4/2003 | Solar et al. | |
| 2003/0074046 A1 | 4/2003 | Richter | |
| 2003/0078606 A1 | 4/2003 | Lafontaine et al. | |
| 2003/0097169 A1 | 5/2003 | Brucker et al. | |
| 2003/0105509 A1 | 6/2003 | Jang et al. | |
| 2003/0114915 A1 | 6/2003 | Mareiro et al. | |
| 2003/0144683 A1 | 7/2003 | Sirhan et al. | |
| 2003/0149468 A1 | 8/2003 | Wallsten | |
| 2003/0153870 A1* | 8/2003 | Meyer | A61M 25/104 604/96.01 |
| 2003/0171799 A1 | 9/2003 | Lee et al. | |
| 2003/0187494 A1 | 10/2003 | Loaldi | |
| 2003/0195609 A1 | 10/2003 | Berenstein et al. | |
| 2003/0199970 A1 | 10/2003 | Shanley | |
| 2003/0199988 A1 | 10/2003 | Devonec et al. | |
| 2003/0208244 A1 | 11/2003 | Stein et al. | |
| 2003/0208255 A1 | 11/2003 | O'Shaughnessy et al. | |
| 2004/0034384 A1 | 2/2004 | Fukaya | |
| 2004/0111108 A1 | 6/2004 | Farnan | |
| 2004/0127475 A1 | 7/2004 | New et al. | |
| 2004/0133223 A1 | 7/2004 | Weber | |
| 2004/0143287 A1* | 7/2004 | Konstantino et al. | 606/194 |
| 2004/0210299 A1 | 10/2004 | Rogers et al. | |
| 2004/0230293 A1 | 11/2004 | Yip et al. | |
| 2004/0243158 A1 | 12/2004 | Konstantino et al. | |
| 2005/0010278 A1 | 1/2005 | Vardi et al. | |
| 2005/0021070 A1 | 1/2005 | Feld et al. | |
| 2005/0021071 A1 | 1/2005 | Konstantino et al. | |
| 2005/0049677 A1 | 3/2005 | Farnan | |
| 2005/0083768 A1 | 4/2005 | Hara | |
| 2005/0131512 A1 | 6/2005 | Vonderwalde | |
| 2005/0137690 A1 | 6/2005 | Salahieh et al. | |
| 2005/0271844 A1 | 12/2005 | Mapes et al. | |
| 2006/0015133 A1 | 1/2006 | Grayzel et al. | |
| 2006/0074484 A1 | 4/2006 | Huber | |
| 2006/0085025 A1 | 4/2006 | Farnan et al. | |
| 2006/0112536 A1 | 6/2006 | Herweck et al. | |
| 2006/0129093 A1 | 6/2006 | Jackson | |
| 2006/0149308 A1 | 7/2006 | Melsheimer et al. | |
| 2006/0173487 A1 | 8/2006 | Uflacker et al. | |
| 2006/0184191 A1 | 8/2006 | O'Brien | |
| 2006/0247674 A1 | 11/2006 | Roman | |
| 2006/0259005 A1 | 11/2006 | Konstantino et al. | |
| 2006/0259062 A1 | 11/2006 | Konstantino | |
| 2006/0270193 A1 | 11/2006 | Hidaka et al. | |
| 2007/0112422 A1 | 5/2007 | Dehdashtian | |
| 2007/0185513 A1 | 8/2007 | Woolfson et al. | |
| 2007/0198047 A1 | 8/2007 | Schon et al. | |
| 2007/0213808 A1 | 9/2007 | Roubin et al. | |
| 2008/0300610 A1 | 12/2008 | Chambers | |
| 2009/0105686 A1 | 4/2009 | Snow et al. | |
| 2009/0105687 A1 | 4/2009 | Deckman et al. | |
| 2009/0264859 A1 | 10/2009 | Mas | |
| 2009/0281490 A1 | 11/2009 | McAuley et al. | |
| 2009/0306582 A1 | 12/2009 | Granada et al. | |
| 2010/0042121 A1 | 2/2010 | Schneider et al. | |
| 2010/0121372 A1 | 5/2010 | Farnan | |
| 2010/0179647 A1 | 7/2010 | Carpenter et al. | |
| 2010/0286720 A1 | 11/2010 | Shaked et al. | |
| 2010/0286721 A1 | 11/2010 | Goodin et al. | |
| 2011/0082483 A1 | 4/2011 | Diamant et al. | |
| 2011/0125247 A1 | 5/2011 | Farnan et al. | |
| 2011/0152905 A1 | 6/2011 | Eaton | |
| 2011/0160756 A1 | 6/2011 | Aggerholm et al. | |
| 2011/0264039 A1 | 10/2011 | Thielen et al. | |
| 2011/0270177 A1 | 11/2011 | Chambers et al. | |
| 2012/0059401 A1 | 3/2012 | Konstantino et al. | |
| 2012/0065660 A1 | 3/2012 | Ferrera et al. | |
| 2012/0215251 A1 | 8/2012 | Burton et al. | |
| 2012/0232638 A1 | 9/2012 | Diamant et al. | |
| 2012/0277626 A1 | 11/2012 | Burbank et al. | |
| 2013/0041391 A1 | 2/2013 | Spencer et al. | |

(56) References Cited

U.S. PATENT DOCUMENTS

| | | |
|---|---|---|
| 2013/0041399 A1 | 2/2013 | Hardert |
| 2013/0060127 A1 | 3/2013 | Burton et al. |
| 2013/0066346 A1 | 3/2013 | Pigott |
| 2013/0096604 A1 | 4/2013 | Hanson et al. |
| 2013/0150874 A1 | 6/2013 | Kassab |
| 2013/0211381 A1 | 8/2013 | Feld |
| 2013/0218181 A1 | 8/2013 | Feld et al. |
| 2013/0226220 A1 | 8/2013 | Konstantino et al. |
| 2013/0253554 A1 | 9/2013 | Gershony et al. |
| 2013/0345730 A1 | 12/2013 | Gershony et al. |
| 2014/0058358 A1 | 2/2014 | Kassab |
| 2014/0066960 A1 | 3/2014 | Feld et al. |
| 2014/0142598 A1 | 5/2014 | Fulton et al. |
| 2015/0100079 A1 | 4/2015 | Moffarah et al. |
| 2016/0331400 A1 | 11/2016 | Gershony et al. |
| 2017/0086877 A1 | 3/2017 | Moffarah et al. |

FOREIGN PATENT DOCUMENTS

| | | | |
|---|---|---|---|
| EP | 1169970 A1 | 1/2002 | |
| EP | 1 179 323 A2 | 2/2002 | |
| EP | 0832608 B1 | 3/2003 | |
| EP | 1042997 B1 | 3/2005 | |
| EP | 1581298 B1 | 8/2006 | |
| EP | 1414373 B1 | 5/2008 | |
| EP | 1337198 B1 | 6/2009 | |
| EP | 1748816 B1 | 7/2010 | |
| EP | 2063924 B1 | 10/2010 | |
| EP | 2283890 A1 | 2/2011 | |
| EP | 1962696 B1 | 3/2012 | |
| EP | 1737530 B1 | 3/2013 | |
| EP | 2564890 A1 | 3/2013 | |
| JP | H06505416 A | 6/1994 | |
| JP | 2002126086 A | 5/2002 | |
| JP | 2002126086 A1 | 5/2002 | |
| JP | 2004504111 A | 2/2004 | |
| JP | 2004148013 A1 | 5/2004 | |
| JP | 2007502694 A | 2/2007 | |
| JP | 2007530158 A | 11/2007 | |
| JP | 2011528963 A | 12/2011 | |
| JP | 2011529350 A | 12/2011 | |
| WO | WO1991002494 A1 | 3/1991 | |
| WO | 9217118 A1 | 10/1992 | |
| WO | WO1993001753 A2 | 2/1993 | |
| WO | WO1994010919 A1 | 5/1994 | |
| WO | WO 9423787 A1 * | 10/1994 | ............ A61M 29/00 |
| WO | WO1994023787 A1 | 10/1994 | |
| WO | WO1994024946 A1 | 11/1994 | |
| WO | WO1995003083 A1 | 2/1995 | |
| WO | WO 98/05377 | 2/1998 | |
| WO | WO 9805377 A1 * | 2/1998 | |
| WO | WO1998045506 A1 | 10/1998 | |
| WO | 1999017680 A1 | 4/1999 | |
| WO | 1999055253 A1 | 11/1999 | |
| WO | 1999062430 A1 | 12/1999 | |
| WO | 02083011 A1 | 10/2002 | |
| WO | WO2002083011 A1 | 10/2002 | |
| WO | WO2003026536 A1 | 4/2003 | |
| WO | WO 03/04176 A2 | 5/2003 | |
| WO | WO2003039628 A2 | 5/2003 | |
| WO | WO2004028610 A2 | 4/2004 | |
| WO | WO2004060460 A2 | 7/2004 | |
| WO | WO2004066852 A2 | 8/2004 | |
| WO | WO2005025458 A1 | 3/2005 | |
| WO | 2009150099 A1 | 12/2009 | |
| WO | 2012040225 A2 | 3/2012 | |
| WO | 2015054277 A1 | 4/2015 | |

OTHER PUBLICATIONS

PCT Search Report for International Application No. PCT/US2002/035547, dated May 20, 2003 by Jacki Tan-Uyen T. Ho.

European search report and search opinion dated May 4, 2010 for EP 06770116.9.

European search report and search opinion dated Dec. 28, 2009 for EP 05792875.6.

Extended European Search Report issued in EP Application No. 11827369.7, dated Apr. 7, 2014. 6 pages.

File History for U.S. Appl. No. 13/044,425, filed Mar. 9, 2011.

First Examination Report dated Feb. 5, 2014 from corresponding EP Application No. 05733012.8.

International search report and written opinion dated Feb. 27, 2007 for PCT/US2006/017872.

International search report and written opinion dated May 23, 2006 for PCT /2005/009571.

International search report and written opinion dated Jul. 26, 2007 for PCT/2005/028809.

International search report and written opinion dated Nov. 4, 2004 for PCT/2004/000177.

International Search Report and Written Opinion issued in PCT/US2011/052392 dated Jan. 11, 2012, 7 pages.

International Search Report issued in PCT/US2002/035547dated May 20, 2003, 3 Pages.

Japanese office action dated Jul. 9, 2010 for JP 2007-505113. (in Japanese with English translation).

Supplementary European Search Report dated Nov. 20, 2013 from corresponding EP Application No. 05733012.8.

*AngioScore, Inc. v. Trireme Medical LLC et al*, Fourth Amended Complaint for: 1) Patent Infringement; 2) Breach of Fiduciary Duty Under California Law; 3) Breach of Fiduciary Duty; Under Delaware Law; 4) Aiding and Abetting a Breach of Fiduciary Duty; and 5) Unfair Competition Under California Business and Professional Cos ss 17200, filed in the United States District Court, Northern District of California, Oakland Division, on Jul. 15, 2014, Case No. 4:12-cv-3393-YGR.

Exhibit A to *AngioScore, Inc. v. Trireme Medical, LLC*, Fourth Amended Complaint filed Jul. 15, 2014, United States District Court, Northern District of California, Oakland Division, Case No. 4:12-cv-3393-YGR.

*AngioScore, Inc. v. Trireme Medical, LLC*, Order Construing Claims in Dispute; Granting in Part and Denying in Part Defendants' Motion for Summary Judgment of Non-Infringment, filed Jun. 25, 2014, United States District Court, Northern District of California, Oakland Division, Case No. 4:12-cv-3393-YGR.

*AngioScore, Inc. v. Trireme Medical, LLC*, Partial Portion of Reporter's Transcript of Proceedings, Sep. 21, 2015, vol. 12, United States District Court, Northern District of California, Oakland Division, Case No. 4:12-cv-3393-YGR (including testimony by Robert Farnan).

*AngioScore, Inc. v. Trireme Medical, LLC*, Partial Portion of Reporter's Transcript of Proceedings, Sep. 22, 2015, vol. 13, United States District Court, Northern District of California, Oakland Division, Case No. 4:12-cv-3393-YGR (including testimony by Ali Almedhychy).

*AngioScore, Inc. v. Trireme Medical, LLC*, Partial Portion of Reporter's Transcript of Proceedings, vol. 14, Sep. 28, 2015, United States District Court, Northern District of California, Oakland Division, Case No. 4:12-cv-3393-YGR (including testimony by Michael Horzewski, jury instructions including meaning of claim terms, and closing arguments).

*AngioScore, Inc. v. Trireme Medical, LLC*, Defendant's Exhibit DX4222, United States District Court, Northern District of California, Oakland Division, Case No. 4:12-cv-3393-YGR (U.S. Pat. No. 5,797,935 to Barath).

*AngioScore, Inc. v. Trireme Medical, LLC*, Defendant's Exhibit DX4224, United States District Court, Northern District of California, Oakland Division, Case No. 4:12-cv-3393-YGR (U.S. Pat. No. 5,868,783 to Tower).

*AngioScore, Inc. v. Trireme Medical, LLC*, Defendant's Exhibit DX4268, United States District Court, Northern District of California, Oakland Division, Case No. 4:12-cv-3393-YGR (U.S. Pat. No. 5,730,698 to Fischell et al.).

*AngioScore, Inc. v. Trireme Medical, LLC*, Defendant's Exhibit DX4272, United States District Court, Northern District of California, Oakland Division, Case No. 4:12-cv-3393-YGR (U.S. Pat. No. 6,059,811 to Pinchasik et al.).

(56) References Cited

OTHER PUBLICATIONS

*AngioScore, Inc.* v. *Trireme Medical, LLC*, Defendant's Exhibit DX4273, United States District Court, Northern District of California, Oakland Division, Case No. 4:12-cv-3393-YGR (U.S. Pat. No. 6,261,319 to Kveen et al.).

*AngioScore, Inc.* v. *Trireme Medical, LLC*, Defendant's Exhibit DX4274, United States District Court, Northern District of California, Oakland Division, Case No. 4:12-cv-3393-YGR (U.S. Pat. No. 6,416,539 to Hassdenteufel).

*AngioScore, Inc.* v. *Trireme Medical, LLC*, Defendant's Exhibit DX4315, United States District Court, Northern District of California, Oakland Division, Case No. 4:12-cv-3393-YGR (Zarge, et al., Chapter 17: Balloon Angioplasty, in Peripheral Endovascular Insterventions (1996)).

*AngioScore, Inc.* v. *Trireme Medical, LLC*, Defendant's Exhibit DX4362, United States District Court, Northern District of California, Oakland Division, Case No. 4:12-cv-3393-YGR, (Palmaz, et al., "Atherosclerotic Rabbit Aortas: Expandable Intraluminal Giafling," Radiology, Sep. 1986, pp. 724-726).

*AngioScore, Inc.* v. *Trireme Medical, LLC*, Defendant's Exhibit DX4473, United States District Court, Northern District of California, Oakland Division, Case No. 4:12-cv-3393-YGR (U.S. Pat. No. 5,196,024 to Barath).

*AngioScore, Inc.* v. *Trireme Medical, LLC*, Verdict Form filed Sep. 29, 2015, United States District Court, Northern District of California, Oakland Division, Case No. 4:12-cv-3393-YGR.

*AngioScore, Inc.* v. *Trireme Medical, LLC*, Judgement as Modified by the Court, filed Oct. 14, 2015, United States District Court, Northern District of California, Oakland Division, Case No. 4:12-cv-3393-YGR.

File History for U.S. Appl. No. 13/022,489, filed Feb. 7, 2011 entitled Balloon Catheter With Non-Deployable Stent.

FFile History for U.S. Appl. No. 12/694,163, filed Jan. 26, 2010 entitled Balloon Catheter With Non-Deployable Stent.

International Preliminary Report on Patentability issued in PCT/US2014/059525, dated Apr. 21, 2016, 5 pages.

*Trireme Medical, LLC* v. *AngioScore, Inc.*, Decision on Appeal dated Feb. 5, 2016, United States Court of Appeals for the Federal Circuit, Case No. 2015-1504.

Extended European Search Report issued in EP Application 14852692.4, dated May 4, 2017, 12 pages.

\* cited by examiner

BALLOON CATHETER WITH NON-DEPLOYABLE STENT

CROSS-REFERENCES TO RELATED APPLICATIONS

This application is a continuation of U.S. application Ser. No. 13/022,489, filed Feb. 7, 2011, which is a continuation of U.S. application Ser. No. 11/292,426, filed Dec. 1, 2005, now U.S. Pat. No. 7,931,663, which is a continuation of U.S. application Ser. No. 10/651,557, filed Aug. 29, 2003, now abandoned, which was a continuation-in-part of U.S. patent application Ser. No. 10/399,589, filed Apr. 18, 2003, now U.S. Pat. No. 7,691,119, which is the U.S. National Stage of PCT Application No. PCT/US02/35547, filed Nov. 6, 2002, which claimed the benefit of U.S. Provisional Application Ser. No. 60/344,982, filed on Nov. 9, 2001, the full disclosures of which are incorporated herein by reference. U.S. application Ser. No. 12/694,163, filed Jan. 26, 2010, as a continuation of U.S. application Ser. No. 10/399,589, filed Apr. 18, 2003, is also a related application.

BACKGROUND OF THE INVENTION

When a balloon used for percutaneous transluminal angioplasty (PTA) or percutaneous transluminal coronary angioplasty (PTCA) is inflated and forced into contact with the plaque, the balloon can have a tendency to move or slip longitudinally in relation to the lesion or the vessel wall being treated.

Cutting balloons (atherotomy) have recently shown clinical efficacy in preventing the reoccurrence of some types of restenosis (specifically calcified lesions and instent restenosis). The cutting balloon is a coronary dilatation catheter with 3 to 4 atherotomes (microsurgical blades) bonded longitudinally on the balloon surface. As the cutting balloon is inflated, the atherotomes move radially and open the occluded artery by incising and compressing the arterial plaque in a controlled manner. An additional advantage of the cutting balloon is that it maintains its position during inflation by using the metal blades on the external surface of the balloon to penetrate into the tissue and prevent the balloon from moving.

Accordingly, it is the principal objective of the present invention to provide a PTA or PTCA balloon that, like a cutting balloon, has a reduced potential of slippage when inflated in a vessel.

DETAILED DESCRIPTION OF THE INVENTION

Figure 1:
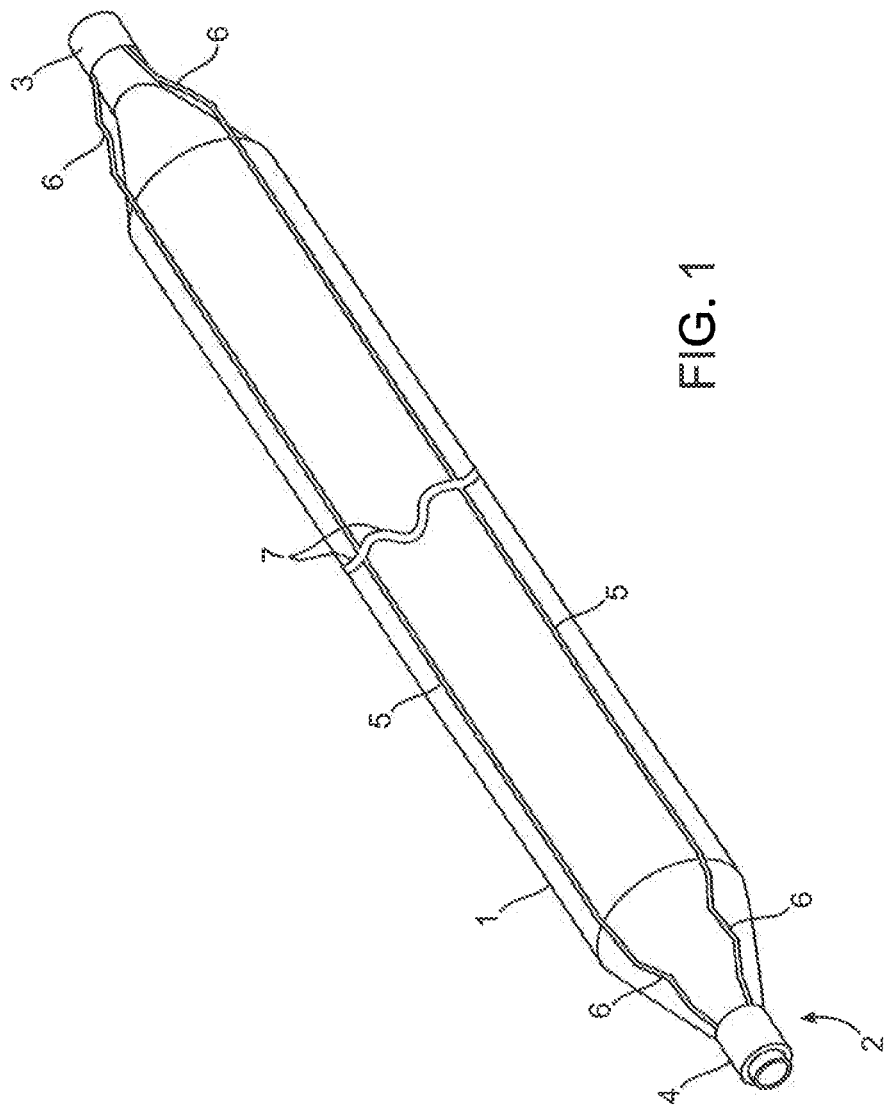
FIG. 1 is a perspective view of an inflated angioplasty balloon incorporating a non-deployable stent according to the present invention.
Figure 2:
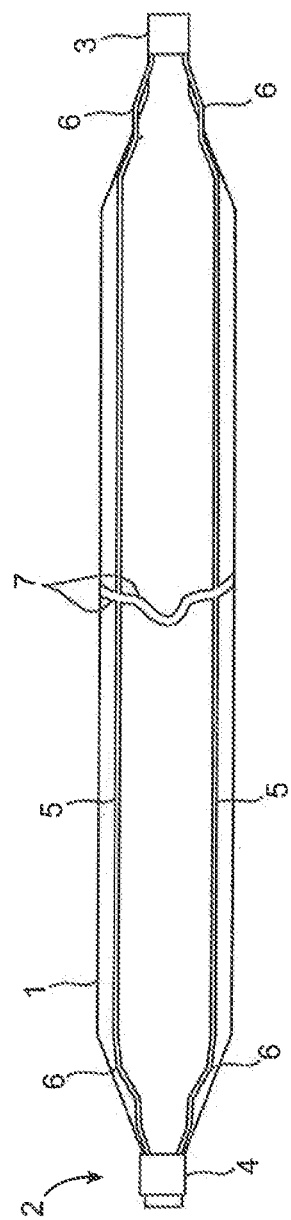
FIG. 2 is a plan view of the inflated angioplasty balloon and non-deployable stent of FIG. 1.

The non-deployable stent of the present invention may be used in conjunction with a conventional balloon catheter, A PTA or PTCA catheter (dilatation catheter) may be a coaxial catheter with inner and outer members comprising a guide wire lumen and a balloon inflation lumen, respectively. Each member can have up to 3 layers and can be reinforced with braids. The proximal end of the catheter has a luer hub for connecting an inflation means, and a strain relief tube extends distally a short distance from the luer hub. The distal ends of the outer and inner members may include a taper. The catheter shaft is built using conventional materials and processes. A catheter having multi-durometer tubing with variable stiffness technology is also a possibility. The catheter should be compatible with a 6F guide catheter. Optionally, the catheter may be a multi-lumen design.

The balloon 1 may be made of either nylon or nylon copolymer (compliant, non-puncture) or PET (high pressure, non-compliant) with a urethane coating to provide tackiness. The balloon may be a multi-layered balloon with a noncompliant inner layer to a most compliant outer layer. For example, an inner most layer of PET, which provides a higher pressure balloon, surrounded by an outer layer of nylon, which provides a more puncture-resistant surface. The balloon may be from 1.5-12 mm in diameter (1.5-4 mm for coronary and 4-12 mm for peripheral vessels) and 15-60 mm in length (15-40 mm for coronary and up to 60 mm for peripheral vessels). The balloon inflation pressure will be from 8-20 atmospheres, depending on the wall thickness of the balloon. When inflated, the balloon ends or necks are cone-shaped.

In keeping with the invention, the balloon is provided with a Nitinol (NiTi) structure, generally designated 2, that incorporates bends for both radial and longitudinal expansion of the Nitinol structure 2 in response to longitudinal and radial expansion of the balloon during inflation, so that the Nitinol structure 2 maintains the balloon in its intended position during inflation. This Nitinol structure 2 can be described as a non-deployable or temporary stent that provides for both controlled cracking of vessel occlusion and gripping of vessel wall during an angioplasty procedure. The Nitinol structure 2 comprises a laser cut hypo tube that expands upon inflation of the balloon, but collapses upon deflation of the balloon because of the super-elastic properties of the Nitinol material, rather than remain expanded in the deployed condition, as would stents in general.

The Nitinol structure or non-deployable stent 2 has a proximal end 3, a distal end 4, and, therebetween, anywhere from 3-12 struts or wires 5 (depending on balloon size—but most likely 3-4 struts) with a pattern of radial and longitudinal bends. The use of laser cutting in connection with stent manufacture is well known (See, e.g., Meridan et al. U.S. Pat. No. 5,994,667), as is the use of the super-elastic nickel-titanium alloy Nitinol (see e.g., Huang et al. U.S. Pat. No. 6,312,459).

As seen in FIGS. 1-4, each end of the four struts 5 has a sinusoidal bend 6 that allows the laser cut hypo tube to expand longitudinally when the balloon 1 is inflated. The linear length of the sinusoidal bends 6 is sized to accommodate the longitudinal expansion of the balloon 1 due to inflation. The strut or wire 5 cross sectional shape can be round, triangular or rectangular. Preferred diameter of the struts 5 ranges from 0.003 to 0.010 inch.

Figure 3:
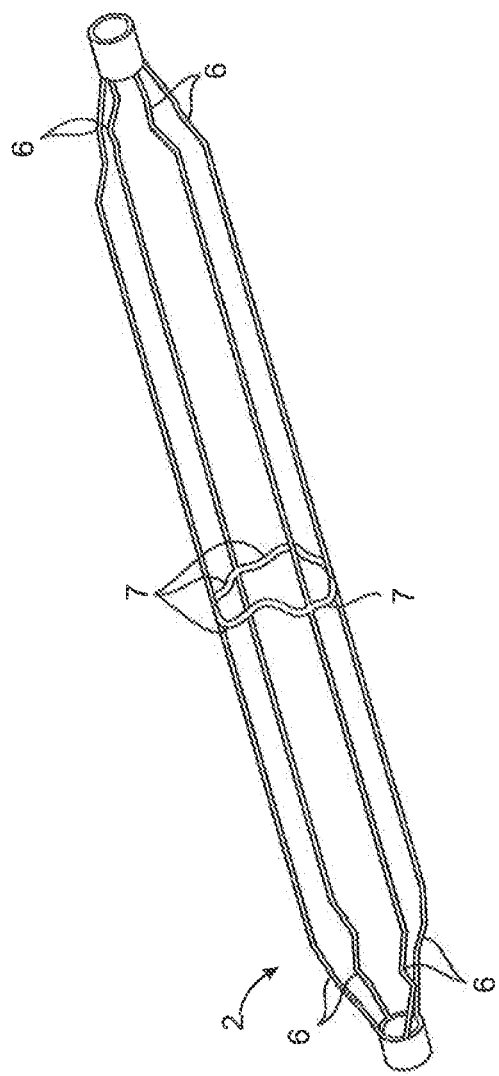
FIG. 3 is a perspective view of the non-deployable stent in its expanded condition, as shown in FIG. 1, with the angioplasty balloon removed so as to more clearly show the stent.
Figure 4:
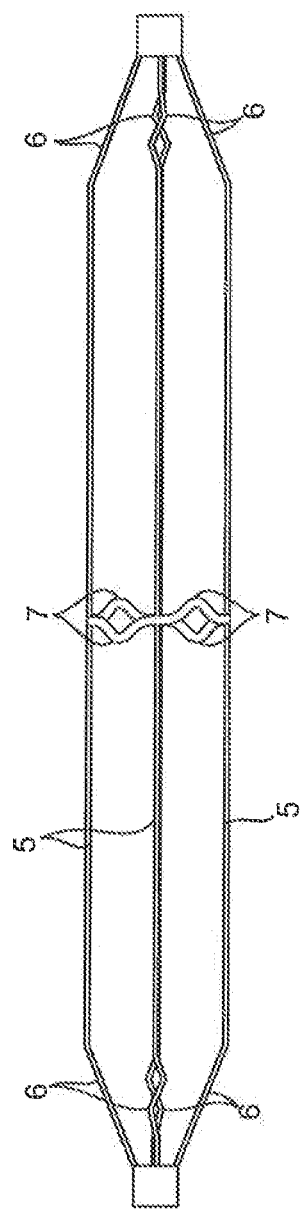
FIG. 4 is a plan view of the non-deployable stent of FIG. 3.
Figure 5:
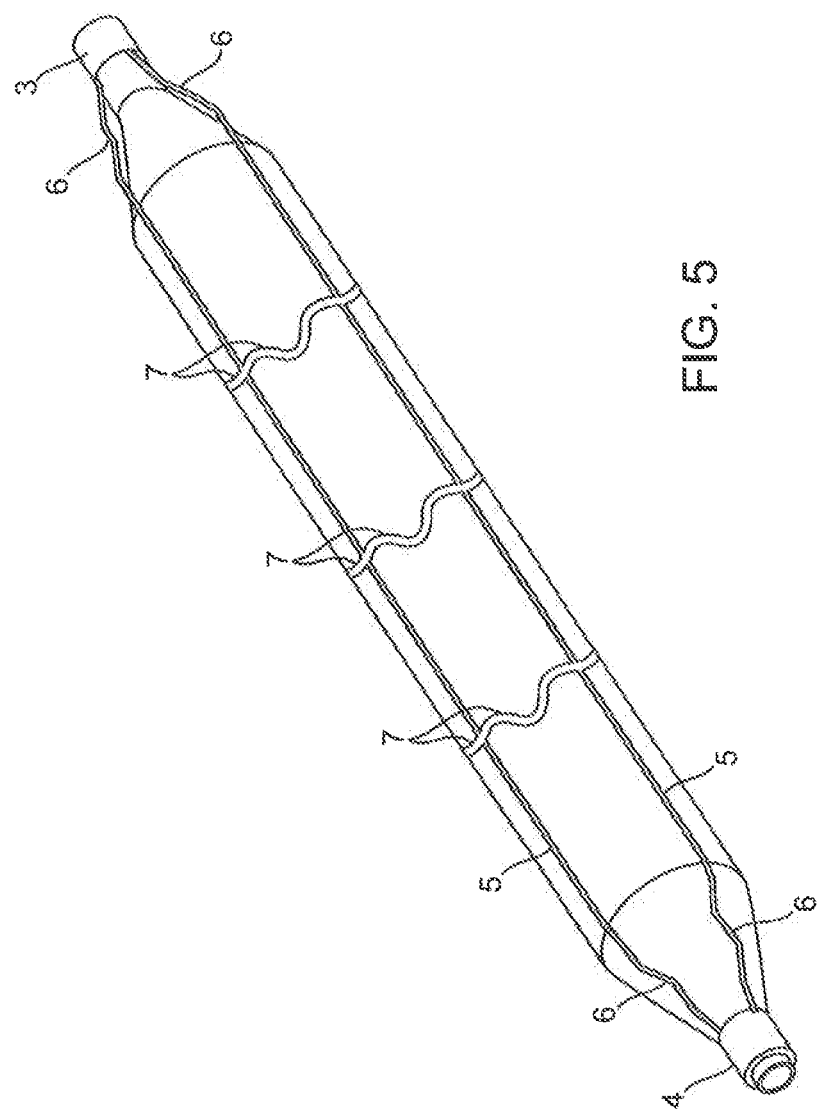
FIG. 5 is a perspective view of an alternate embodiment of the non-deployable stent associated with an angioplasty balloon that has a longer working length than the angioplasty balloon shown in FIGS. 1 and 2.

At the longitudinal center of the hypo tube, a U-shaped circumferential connector 7 joins each strut 5 to its adjacent strut. As best seen in FIGS. 3 and 4, the U-shaped connectors 7 are on opposing sides of the central radial axis, and connectors 7 are joined to struts 5 at intersecting angles of 90 degrees. The distal end 4 of the hypo tube is adhered to the distal neck of the balloon or the distal end of the catheter shaft, and the proximal end 3 of the hypo tube is either attached to the proximal neck of the balloon or to the proximal end of the catheter shaft. The struts 5 may be attached to the working region of the balloon 1 to assist the hypo tube in staying with the balloon as it inflates and deflates, and an adhesive, such as a cyanoacrylate adhesive, may be used to tack the struts down onto balloon at various points.

Catheter shafts to which the balloon and laser cut hypo tube are attached can have diameters ranging from 2.5F to 8F, and the distal end may be tapered and slightly less in diameter than the proximal end.

Figure 6:
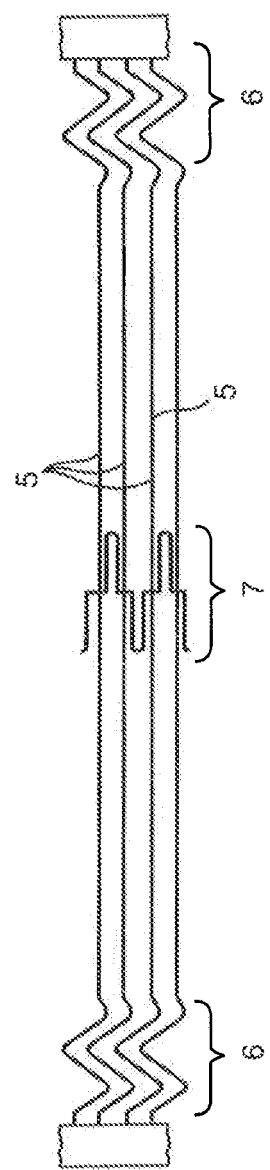
FIG. 6 is an engineering drawing showing, in plan view, the layout of a non-deployable stent adapted to be used with an angioplasty balloon of 20 mm in length. (All dimensions shown in the drawing are in inches.)

In FIG. 6, the dimensions of the laser cut hypo tube are for use with a 3 mm (0.118 in) diameter by 20 mm length balloon. The circumference of a 3 rom balloon is nD=3.14(3 mm) 9.42 mm or 0.37 in. As can be readily appreciated, the total length of all U-shaped connectors 7 (up and back) must be greater than the circumference of the inflated balloon 1. The length of each U-shaped connector 7 (up and back), may be calculated using the following equation: where d is the diameter of the inflated balloon and n is the number of struts. The total length of the U-shaped bends (up and back) must exceed this length.

The resulting number is divided by 2 to get the length which each up-and-back side of the U-shaped connector should exceed. For example: for a 3 mm balloon compatible, laser-cut hypo tube with four struts, the length of each U-shaped connector (up and back) is 0.37 inch divided by 4=0.0925 in. Further divide by 2 and to get 0.04625 in. This is the length that each side of the U-shaped connector must exceed.

Figure 7:
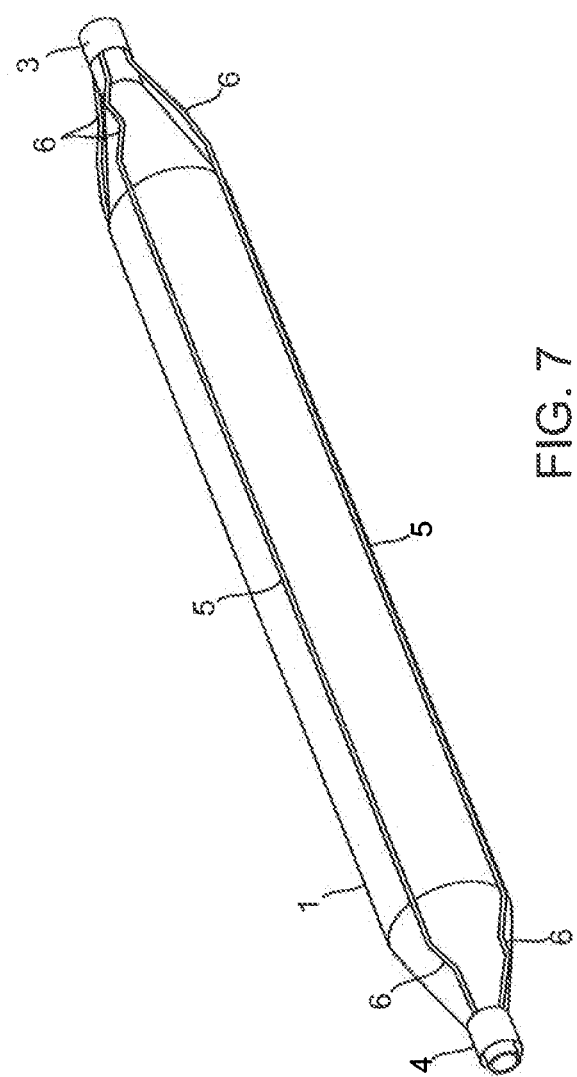
FIG. 7 is a perspective view of an inflated angioplasty balloon incorporating an alternative embodiment of a non-deployable stent which does not include any connecting elements between the struts intermediate the ends of the balloon.
Figure 8:
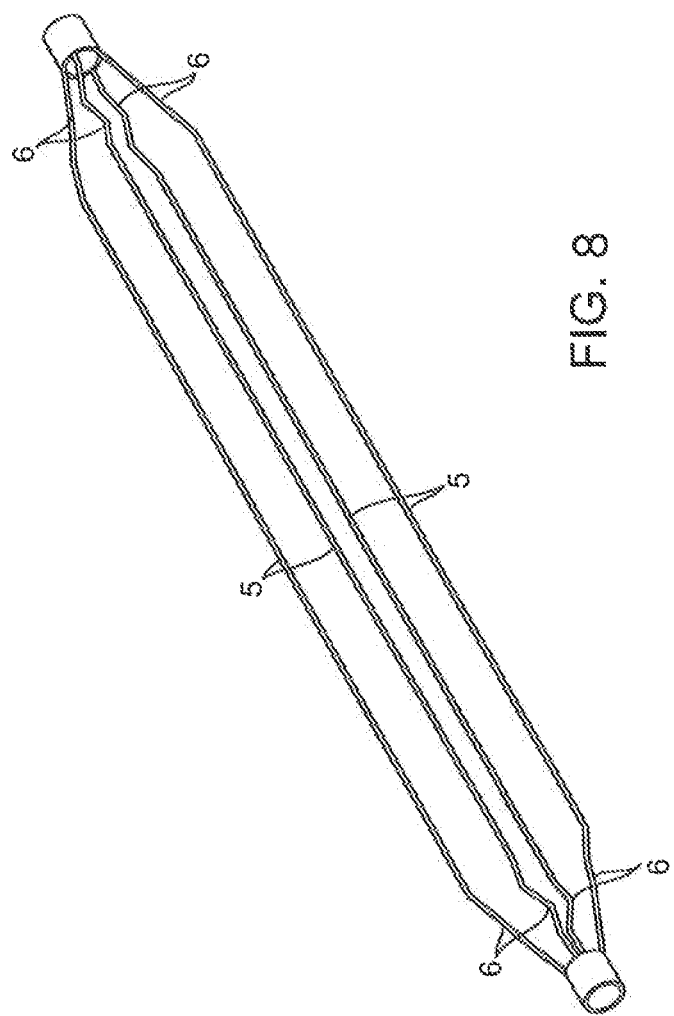
FIG. 8 is a perspective view of the non-deployable stent shown in FIG. 7, with the angioplasty balloon removed so as to more clearly show the stent.
Figure 9:
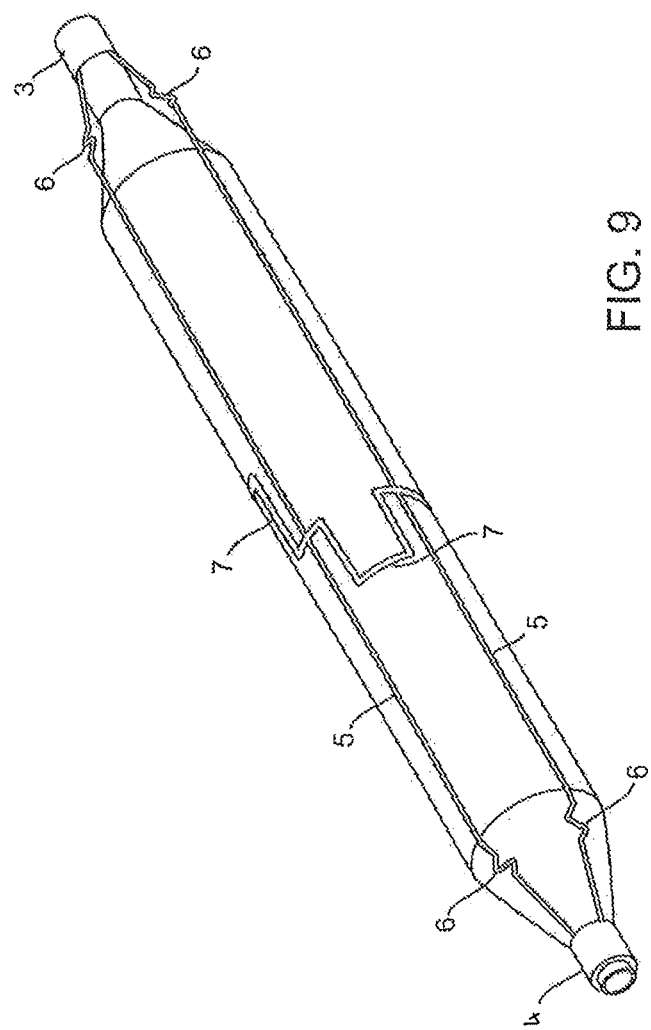
FIGS. 9 and 10 are perspective views similar to FIGS. 1, 5, and 7 showing a further embodiment of the invention.
Figure 10:
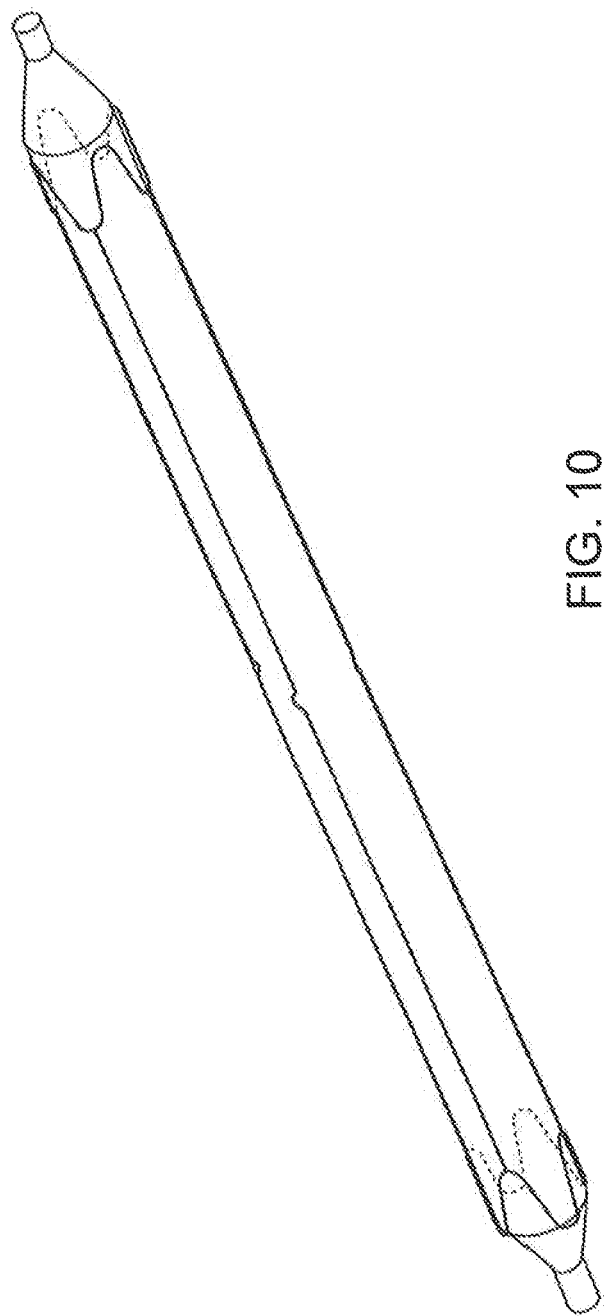
Figure 11:
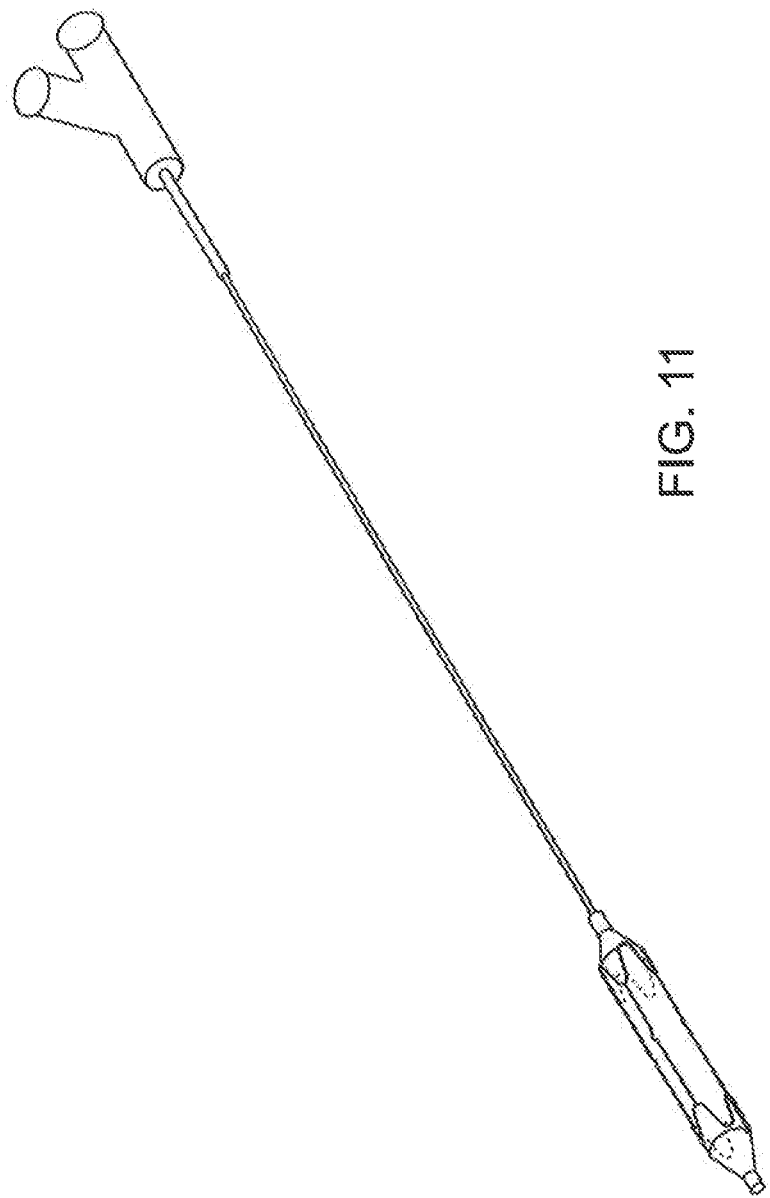
FIG. 11 is a perspective view of a further embodiment of the present invention showing the balloon and non-deployable stent in conjunction with a catheter.

There is also one or more sets of U-shaped connectors 7 in between the sinusoidal bends 6. The set includes one U-shaped connector for each strut (3 struts—a set of 3 U-shaped connectors; 4 struts—a set of 4 U-shaped connector; and so on). The number of U-shaped connector sets depends on the length of the balloon and thus, the length of the laser cut hypo tube. For a 20 mm length balloon, there is one set of U-shaped connectors spaced 10 mm from the end (at the halfway point along length of balloon). For a 40 mm length balloon, there are three sets of U-shaped connectors spaced in 10 mm increments (the first set is spaced 10 mm from one end; the second set is spaced 10 mm from first set; and the third set is spaced 10 mm from each the second set and the other end). The equation for number of sets of U-shaped connectors.

$$\frac{L}{10} - 1$$

where L=length of balloon in mm. Other embodiments, such as those shown in FIGS. 7 and 8, do not incorporate the intermediate U-shaped connectors.

Figure 12:
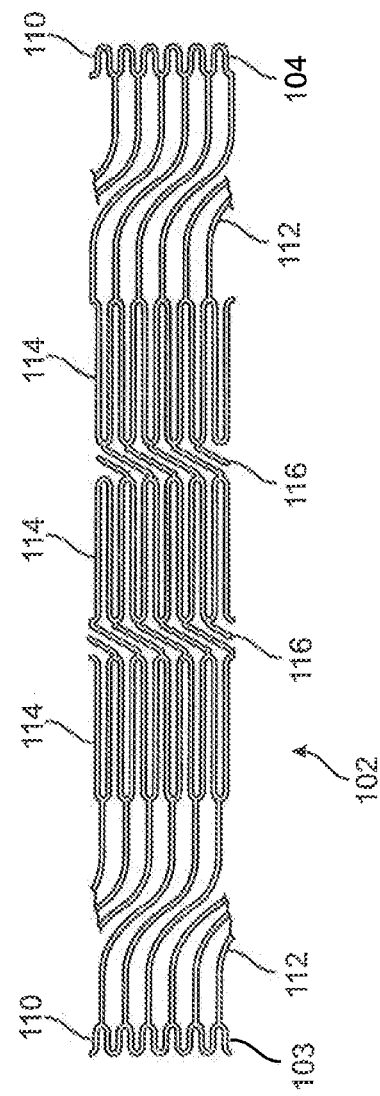
FIG. 12 is an engineering drawing showing, in plan view, the layout of another embodiment of a non-deployable stent adapted to be used with an angioplasty balloon, in accordance with the present invention.

FIG. 12 is directed to another embodiment of a non-deployable stent 102 which can be used with a conventional balloon catheter, in accordance with the present invention. The stent of this embodiment preferably has a Nitinol structure, though other materials can be used as discussed supra, that incorporates bends for both radial and longitudinal expansion of the stent in response to radial and longitudinal expansion of the balloon during inflation, so that the stent 102 maintains the balloon in its intended position. Similar to the stents of the other embodiments of the present invention discussed supra, the stent comprises a laser cut hypo tube that expands upon inflation of the balloon and collapses upon deflation of the balloon. Further, the stent is preferably secured to the balloon with some type of anchoring means. Preferably, such anchoring means are utilized at the ends of the stent and around the neck of the balloon. Examples of such anchoring means are utilized at the ends of the stent and around the neck of the balloon. Examples of such anchoring means include an adhesive such as for example a UV adhesive, cyanoacrylate, or a two-part epoxy, RF heat welding, solvent bonding, or crimping or swaging the ends of the stent to the shaft. Alternatively, a mechanical anchoring means can be used to anchor the stent to the balloon. With such a means, a small sleeve made of a similar material as the shaft of the catheter is mounted over the ends of the stent and heat welded together where the ends of the stent are sandwiched between the shaft and the sleeve.

FIG. 12 shows the hypo tube of the stent in an unrolled (flat) and non-extended state. The stent 102 has a proximal end 103 and a distal end 104. At each end, there are cage mounted flanges 110. These flanges can be used to attach the stent to the neck of the balloon. The flanges also spring open radially to permit insertion of the balloon during assembly. Between the ends, the stent 102 includes extension sections 112, serpentine rings 114 and elongation links 116.

Serpentine rings 114 have a serpentine shape and allow the stent 102 to expand radially when a balloon in the stent is inflated. However, as the balloon expands, the serpentine rings 114 will shorten in length. Accordingly, extension sections 112 and elongation links 116 expand longitudinally to compensate for any shortening of the length of the serpentine rings 114. Preferably, elongation links 116 have a z-shape, s-shape or accordion shape, as shown in FIG. 12.

Figure 13:
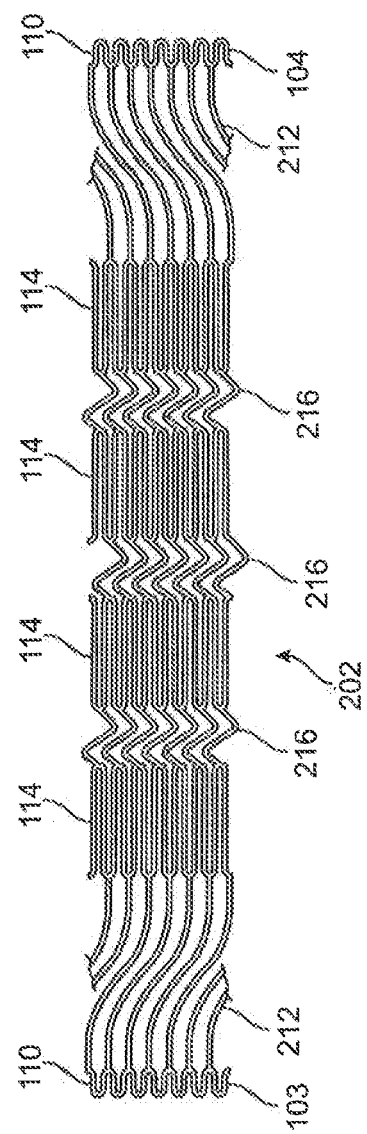
FIG. 13 is an engineering drawing showing, in plan view, the layout of an alternate non-deployable stent of the embodiment in FIG. 12.

FIG. 13 is an alternative embodiment showing a stent 202 having the same features as the stent in FIG. 12 except that stent 202 in FIG. 13 has elongated links 216 with a different pattern than the elongated links 116 in stent 102 of FIG. 12. More specifically, elongated links 216 have a zig zag pattern. Stent 202 of FIG. 13 operates in a substantially similar manner to that of stent 102 in FIG. 12.

While the present invention is not limited in the number of serpentine rings, extension sections and elongated links used in the stent, FIG. 13 illustrates a preferred embodiment. The stent 202 in FIG. 13 has from proximal end 103 to distal end 104, a first extension section 112, a first set of serpentine rings 114, a first set of elongated links 216, a second set of serpentine rings 114, a second set of elongated links 216, a third set of serpentine rings 114, a third set of elongated links 216, a fourth set of serpentine rings 114, and a second extension section 112.

FIG. 13 also shows an example of possible dimensions, in inches, of each of the components of the stent 202. These dimensions would also be used for each of the similar components in stent 102 in FIG. 12.

It will be understood that the embodiments and examples of the present invention, which have been described, are illustrative of some of the applications of the principles of the present invention. Numerous modifications may be made by those skilled in the art without departing from the true spirit and scope of the invention.

What is claimed is:

1. A system for performing angioplasty, said system comprising:
    a catheter shaft having a distal end and an inflatable balloon disposed adjacent the distal end, wherein the inflatable balloon comprises a working length; and
    an expandable constraining structure disposed over the inflatable balloon, wherein the expandable constraining structure comprises a plurality of axial struts and at least one ring, wherein each of the axials struts comprise a central portion, wherein the ring is disposed over the working length of the inflatable balloon and intersects the central portions of the axial struts, said expandable constraining structure having a non-expanded configuration and an expanded configuration, wherein the non-expanded configuration comprises the expandable constraining structure lying closely over the inflatable balloon prior to inflation of the inflatable balloon, wherein the expanded configuration comprises the expandable constraining structure being smaller than an unconstrained size of the expandable balloon upon inflation of the inflatable balloon so that the expandable constraining structure restrains the inflatable balloon along a plurality of crossing channel lines, wherein the axial struts are joined to the catheter on a distal side of the balloon and a proximal side of the balloon wherein both ends of said constraining structure are fixedly attached to the catheter shaft.

2. A system as in claim 1, wherein the channel lines are oriented axially, circumferentially, or both axially and circumferentially.

3. A system as in claim 2, wherein the expandable constraining structure comprises a multiplicity of axially spaced-apart radially expandable rings attached to the axial struts, wherein the axial struts are circumferentially spaced-apart and cross the radially expandable rings.

4. A system as in claim 3, wherein the rings are joined to the struts at intersecting angles of 90°.

5. A system as in claim 3, wherein the radially expandable rings are composed of an elastic material which can elongate to allow the rings to expand when the inflatable balloon is inflated.

6. A system as in claim 5, wherein the radially expandable rings are formed with deformable features which allow their radial expansion when the balloon is inflated.

7. A system as in claim 6, wherein the deformable features comprise one or more of zig-zags, S-curves, and coils.

8. A system as in claim 1, wherein the axial struts are each elastic in tension so that they will elongate as the inflatable balloon inflates.

9. A method for treating a lesion in a blood vessel, said method comprising:
    inflating a balloon and expanding an expandable constraining structure, within the blood vessel, wherein the expandable constraining structure comprises a plurality of circumferentially spaced-apart axial struts and a plurality of axially spaced-apart radially expandable rings wherein the axial struts cross the rings, thereby creating openings in the expandable constraining structure, the plurality of axially spaced-apart radially expandable rings comprising a distal ring, a proximal ring and an intermediate ring between the distal ring and proximal ring, wherein the axial struts are joined to the catheter on a distal side of the balloon and a proximal side of the balloon; wherein both ends of said constraining structure are fixedly attached to the catheter shaft; and
    constraining the balloon inflation along a plurality of crossing channel lines formed by said axial struts and said rings, whereupon inflation of the balloon, the expandable constraining structure has a configuration smaller than an unconstrained size of the balloon.

10. A method as in claim 9, wherein the balloon is composed of a non-distensible or semi-compliant material and is inflated to a pressure in the range from 10 atm. to 25 atm.

11. A method as in claim 9, wherein the balloon is constrained along crossing axial and circumferential channel lines to form quadrangular isolated protruding regions.

12. A method as in claim 9, wherein a plurality of protruding regions have similar sizes and are uniformly distributed over the balloon surface.

13. A system for performing angioplasty, said system comprising:
    a catheter shaft having an inflatable balloon adjacent its distal end; and
    an expandable constraining structure disposed over the inflatable balloon, wherein both ends of said constraining structure are directly affixed attached to the catheter shaft, the expandable constraining structure comprising a plurality of circumferentially spaced-apart axial struts and a plurality of axially spaced-apart radially expandable rings coupled to the axial struts, the plurality of axially spaced-apart radially expandable rings comprising a distal ring, a proximal ring and an intermediate ring between the distal ring and proximal ring, wherein a portion of the axial struts is un-affixed to the inflatable balloon, wherein the axial struts cross the radially expandable rings, wherein the expandable constraining structure comprises a non-expanded configuration and an expanded configuration, wherein the expandable constraining structure is in the non-expanded configuration when the inflatable balloon is in a deflated state and the expandable constraining structure is in the expanded configuration when the inflatable balloon is in an inflated state, whereupon the expandable constraining structure being in the non-expanded configuration, the expandable constraining structure lies closely over the inflatable balloon, and whereupon the expandable constraining structure being in the expanded configuration, the expandable constraining structure restrains inflation of the inflatable balloon along the axial struts.

14. The system of claim 13, whereupon the expandable constraining structure being in the non-expanded configuration, the expandable constraining structure comprises a different configuration than the inflatable balloon in the deflated state.

15. The system of claim 14, whereupon the expandable constraining structure being in the expanded configuration, the expandable constraining structure comprises a different configuration than the inflatable balloon in the inflated state.

16. The system of claim 13, whereupon the expandable constraining structure being in the expanded configuration, the expandable constraining structure comprises a different configuration than the inflatable balloon in the inflated state.

17. A system as in claim 3, wherein the multiplicity of axially spaced-apart radially expandable rings comprises a distal ring, a proximal ring and an intermediate ring between the distal ring and proximal ring and the intermediate ring is the at least one ring.

18. A system as in claim 17, wherein the distal ring, the proximal ring and the intermediate ring are disposed over a working length of the inflatable balloon.

\* \* \* \* \*